United States Patent
Cain et al.

(10) Patent No.: US 8,518,413 B2
(45) Date of Patent: Aug. 27, 2013

(54) PROBIOTIC BACTERIAL STRAINS FOR USE TO DECREASE MORTALITY IN FISH DUE TO BACTERIAL DISEASE

(75) Inventors: Kenneth Cain, Moscow, ID (US); David Burbank, Carson, WA (US)

(73) Assignee: University of Idaho, Moscow, ID (US)

( * ) Notice: Subject to any disclaimer, the term of this patent is extended or adjusted under 35 U.S.C. 154(b) by 0 days.

(21) Appl. No.: 13/425,491

(22) Filed: Mar. 21, 2012

(65) Prior Publication Data

US 2012/0258138 A1     Oct. 11, 2012

Related U.S. Application Data

(60) Provisional application No. 61/516,626, filed on Apr. 5, 2011.

(51) Int. Cl.
| | |
|---|---|
| *A61K 35/74* | (2006.01) |
| *C12N 1/20* | (2006.01) |
| *A61P 31/04* | (2006.01) |

(52) U.S. Cl.
USPC ..... 424/234.1; 424/93.1; 435/243; 435/252.1

(58) Field of Classification Search
None
See application file for complete search history.

(56) References Cited

U.S. PATENT DOCUMENTS

| 5,284,653 | A | 2/1994 | Wolf-Watz |
| 6,881,412 | B1 | 4/2005 | Shoemaker |
| 6,991,793 | B2 | 1/2006 | Shoemaker |
| 7,067,122 | B1 | 6/2006 | Evans |
| 2006/0073167 | A1 | 4/2006 | Oshima |
| 2008/0171064 | A1 | 7/2008 | Mizuno |

OTHER PUBLICATIONS

Balcazar, JL, "The Role of Probiotics in Aquaculture," Veterinary Microbiology, 114:173-186 (2006).
Gatesoupe, JF, "Probiotics and Prebiotics for Fish Culture, at the Parting of the Ways," Aqua Feeds:Formulation & Beyond, 2(3):3-5 (2005).
LaFrentz, BR, "Bacterial Coldwater Disease," An Extension Bulletin for the Western Regional Aquaculture Center (2004).
Taghavi, S. "Genome Sequence of the Plant Growth Promoting Endophytic Bacterium Enterobacter sp. 638," PLOS Genetics, 6(5): e1000943. doi:10.1371/journal.pgen.1000943 (2010).

*Primary Examiner* — Robert A Zeman
(74) *Attorney, Agent, or Firm* — Howard Eisenberg, Esq.

(57) ABSTRACT

Two novel strains of bacteria, C6-6 and C6-8, deposited in accordance with the Budapest Treaty, protect fish, such as by reducing mortality, against disease caused by bacteria, such as coldwater disease caused by *Flavobacterium psychrophilum*.

7 Claims, 2 Drawing Sheets

PROBIOTIC BACTERIAL STRAINS FOR USE TO DECREASE MORTALITY IN FISH DUE TO BACTERIAL DISEASE

This application claims priority from pending U.S. Provisional Patent Application Ser. No. 61/516,626, filed on Apr. 5, 2011, which application is incorporated herein in its entirety.

It is hereby acknowledged that the U.S. Government has certain rights in the invention described herein, which was supported in part by United States Department of Agriculture contract numbers: 103306G0017310; 113389G0025555; 111033G002502.

FIELD OF THE INVENTION

This invention pertains to the field of protection of fish from disease caused by bacteria. In one embodiment, the invention pertains to the protection of fish from disease caused by bacteria by administering to the fish one or more probiotic organisms. In a particular embodiment, the invention pertains to the field of the use of probiotic organisms to protect fish from disease caused by bacteria such as *Flavobacterium psychrophihun* and *F. columnare*.

BACKGROUND OF THE INVENTION

The use of probiotics to increase disease resistance and improve the overall health of terrestrial animals has long been established. However, their use and effectiveness in aquaculture environments has only recently been recognized.

*Flavobacterium psychrophilum* is the causative agent of coldwater disease (CWD) as well as rainbow trout fry syndrome (RTFS). While all salmonids are susceptible to *F. psychrophilum*, rainbow trout *Oncorhynchus mykiss* are especially affected, as observed through economic loss to aquaculture operations. Currently, no commercial vaccine exists for *F. psychrophilum*, leaving antibiotics as the primary form of treatment. While new antibiotic treatments such as florfenicol have recently been approved for control of CWD, there is continued concern over antibiotic use due to the potential development of bacterial resistance. Consequently, the use of a probiotic to decrease morbidity and mortality due to infectious disease, such as that caused by *F. psychrophilum*, would be useful as a potential method to reduce the use of traditional antibiotics in combating this and other microorganisms.

While the mechanisms allowing a particular probiotic to improve health are not always clear, the observed probiotic modes of action have been shown to include the production of inhibitory compounds, competitive exclusion, improvement of the immune response, and possible enhancement of water quality. While many definitions have been established to describe probiotics, several characteristics, including survival and colonization of the gastrointestinal tract are noted as important characteristics of probiotic selection. Additionally, an effective probiotic should not directly cause mortality in the animal that it is intended to be used in. Other desirable characteristics of effective probiotics for use in aquatic animals include non-pathogenicity to both the host and humans, resistance to bile salts, pH tolerance, antagonism towards the pathogen of interest, the ability to adhere to and colonize the intestine of the host, strong growth characteristics, and autochthonous to the host or its environment.

DETAILED DESCRIPTION OF THE INVENTION

Figure 1:
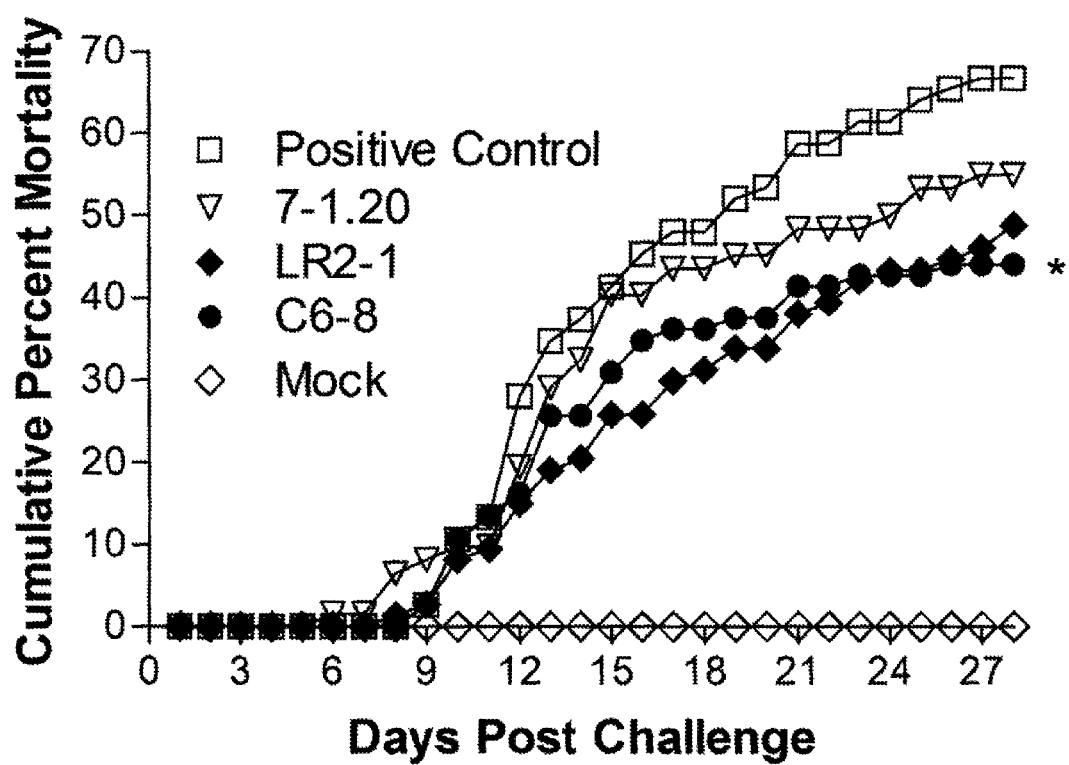
FIG. 1 is a graph showing % survival plotted against days post challenge for mock infected fish ($\diamond$) and for fish exposed to pathogenic *Flavobacterium psychrophilum* and then fed a feed containing candidate probiotic strain C6-8 ($\bullet$), LR2-1 ($\blacklozenge$), or 7-1.20 ($\triangledown$). Positive control ($\square$). * indicates significantly different from positive control ($p<0.05$).

In one embodiment, the invention is an isolated strain of bacteria selected from the group consisting of C6-6 *Enterobacter* sp. and C6-8 *Enterobacter* sp. Each of these two bacterial strains was deposited at the Agricultural Research Service Culture Collection (USDA, ARS, 1815 North University Street, Peoria, Ill., 61064) on Mar. 23, 2011. The deposits were made under the terms of the Budapest Treaty. "C6-6" has been assigned Accession number NRRL No. B-50481 and "C6-8" has been assigned Accession number NRRL No. B-50482.

The deposited bacterial strains are useful, individually or in combination with each other or with one or more other bacterial strains, as a probiotic for the treatment and prophylaxis or prevention of infectious diseases, such as coldwater disease, in salmonids.

These two strains of bacteria were selected from a total of 318 isolates that were collected from rainbow trout. Of these 318 isolates obtained, 84 could not be re-grown from frozen stock and were eliminated from further testing. The remaining 234 isolates were screened against *F. psychrophilum* in vitro. Of these 234 isolates, 24 exhibited inhibitory activity against *F. psychrophilum*. Each of these 24 isolates was tested and was found to be able to survive a 1.5 hour exposure to 10% rainbow trout bile. Of the 24 isolates evaluated, eight were observed to cause direct mortality when injected into fish and were therefore eliminated from further consideration as a probiotic. Of the remaining 16 isolates, 8 were found to be unsuitable for use as a probiotic for various other reasons, leaving 8 from the original 318 isolates.

As discussed in more detail below, the remaining eight candidate probiotic bacteria were tested in in vivo tests for their ability to decrease mortality in fish due to *F. psychrophilum*. After a 28 day challenge, two of the candidate bacterial strains, referred to herein as "C6-6" and "C6-8" were shown to significantly decrease mortality in fish due to *F. psychrophilum* infection.

In another embodiment, the invention is a method for protecting fish, such as decreasing mortality, from a bacterial disease, such as coldwater disease caused by *Flavobacterium psychrophilum* bacteria. In accordance with this embodiment of the invention, a fish that is susceptible to a bacterial disease such as coldwater disease is administered either or both of C6-6 or C6-8 in an amount sufficient to decrease mortality of fish due to bacterial diseases, such as coldwater disease caused by *Flavobacterium psychrophilum*.

Fish that are suitable for the method of the invention include any fresh or saltwater fish that is susceptible to disease caused by a bacterium such as *Flavobacterium psychrophilum*. Such fish include salmonids, such as salmon and trout species. Examples of suitable fish for the method of invention include salmonids (*Oncorhynchus* sp. and *Salmo* sp.), American, European, and Japanese eels (*Anguilla* sp.), tilapia (*Oreochromis* sp.), striped bass and hybrid-striped bass (*Mor-* one chrysops and *M. saxalilis*), flounders (*Seriola* sp.), seabream (*Sparus* sp.), sea perch (*Lates calcarifer*), the estuarine grouper (*Epinephelus tawine*), walleye (*Stilzostedion vitreum*), channel catfish (*Ictalurus punctutus*), centrachids (such as largemouth bass, *Micropterus salmoides*), brown bullheads (*Nebulosus* sp.), fat head minnows (*Pimephales promelas*), golden shiners (*Netemigonus crysoleucas*), goldfish (*Carassius auratus*), carp (*Cyprinus carpio*), and aquarium fish species such as black mollies (*Poecilia sphenops*) and platies (*Xiphophorus maculatus*). Species affected specifically by CWD include all salmonids. The pathogen has also been reported in non-salmonid species, such as eel *Anguilla* sp., sea lamprey *Petromyzon marinus*, carp *Cyprinus carpio*, tench *Tinca tinca*, crucian carp *Carassius carassius*, goldfish *C. auratus*, ayu *Plecoglossus altivelis*, pale chub *Zacco platypus*, perch *Perca fluviatilis*, and roach *Rutilus rutilus*.

The bacterial strains of the present application may be administered to the fish in various ways. For example, the strains may be introduced into the gastrointestinal tract, such as by diet supplementation. Spraying or top dressing the feed with the strains may be utilized to include the strains into the diet.

Alternatively, or in addition to feed supplementation, strains may be introduced into susceptible fish by immersion of the fish into water containing high levels of the strains. In a less preferred method, the strains may be introduced into fish by injection or gastric gavage. These latter methods are less preferred because such protocols require individual handling of fish and, therefore, they are less suitable for most aquaculture applications method of utilization of probiotics.

The amount of bacterial organisms that are delivered to the fish is an amount that is effective to provide protection, such as decreasing mortality, against disease, such as that caused by *Flavobacterium psychrophilum*. For example, if the bacterial strains are introduced into fish by diet supplementation, the probiotic bacteria may be added at a concentration between $10^3$ to $10^{10}$ bacterial cells per gram of feed. If desired, concentrations lower than $10^3$ bacterial cells per gram of feed or higher than $10^{10}$ bacterial cells per gram of feed may be utilized.

Either of strain C6-6 or strain C6-8 may be introduced into the fish or both strains C6-6 and C6-8 may be introduced in combination into the fish in accordance with the method of the present application. In accordance with the method of the application, either or both strains may be introduced into the fish together with other bacterial species, if desired. Such other bacterial species may or may not provide additional benefits to the fish, such as increased resistance to bacterial disease such as coldwater disease.

The invention is further illustrated in the following non-limiting examples. It is noted that the examples utilize *Flavobacterium psychrophilum* as an illustration of an infectious agent that causes a disease that results in mortality in fish and for which the rate of mortality is significantly reduced by the administration to fish of one or both of the probiotic organisms of the present application. Because it is understood by those of skill in the art that the probiotics disclosed herein are not closely related to *F. psychrophilum* and that the beneficial effects of probiotics in combating the deleterious effects of an infectious disease do not pertain to a specific relationship between any particular pathogenic microorganism and the probiotic microorganism, one of skill in the art would understand that the description herein pertaining to *F. psychrophilum* and coldwater disease is merely illustrative and that the probiotics disclosed herein would confer beneficial results with regards to infectious diseases other than coldwater disease.

In the following examples, statistical analyses were performed as follows. Survival curves for pathogenicity tests were generated and compared to control tanks using the log-rank (Mantel-Cox) test (Peto and Peto, Journal of the Royal Statistical Society A, 135 part 2:185-207 (1972)) with differences considered significant at p-value<0.05. All statistical analyses of data were completed using GraphPad Prism® 5.02 software (GraphPad Software Inc., La Jolla, Calif.). Following the 28 day challenge, mean cumulative percent mortality was analyzed using a one way analysis of variance (ANOVA) with pairwise comparisons made using a Tukey's post test. Differences were considered significant at p-values<0.05. Survival curves were generated to analyze mortality rate by the Kaplan-Meier method (Kaplan and Meier, Journal of the American Statistical Association, 53:457-481 (1958) and compared to control tanks using the log-rank (Mantel-Cox) test with differences considered significant at p-value<0.05. All statistical analyses of data were completed using GraphPad Prism 5.02 software.

EXAMPLE 1

Fish Collection and Bacterial Isolation from GI Tract

Twenty nine rainbow trout were collected from the University of Idaho Aquaculture Research Institute (Moscow, Id.), two commercial trout fish hatcheries, and Spring Valley Reservoir (Troy, Id.). Bacteria from the GI tract were removed and cultured based on methods described in Spanggaard et al, Aquaculture, 182:1-15 (2000). Briefly, fish were euthanized using an overdose of tricaine methanesulfonate (MS222®, Argent Chemical Laboratories, Inc., Redmond, Wash.). After aseptically removing the mid and hind portions of the intestine (up to the pyloric caeca), the intestinal contents were expelled by squeezing and washing with 1× sterile phosphate-buffered saline (PBS) and placed into a STOMACHER® bag (Seward Laboratory Systems Inc., Port St. Lucie, Fla.). The intestinal contents were then homogenized for 30 seconds with 2 ml of sterile 1×PBS. Each homogenized gut sample was plated (200 μl) in triplicate on tryptic soy agar (TSA) and tryptone yeast extract and salts (TYES) agar plates and incubated for 5 to 7 days at 15° C. After incubation, each differentiated colony that grew was subcultured onto culture plates containing the appropriate media for isolation (TSA or TYES). Once isolation was achieved, single colonies were picked using a sterile swab and swirled in 2 ml cryovials containing 1 ml of sterile 20% glycerol. The isolates were then stored in duplicate at −80° C. for further screening.

A total of 318 isolates were collected from the fish sampled. Of the 318 isolates obtained, 84 could not be re-grown from frozen stock and were eliminated from further testing.

EXAMPLE 2

In vitro Screening Against *F. psychrophilum*

The 234 isolates of Example 1 that showed growth following storage were screened against *F. psychrophilum* in vitro based on methods described in Gram and Melchiorsen, Journal of Applied Bacteriology, 80:589-595 (1996). Four days prior to screening, 10 ml of TYES broth was inoculated with a known virulent strain of *F. psychrophilum* (CSF 259-93), while the isolate to be screened was inoculated two days prior to screening in 10 ml of its respective broth media. Aliquots (2 ml) of each isolate and a 2 ml aliquot of *F. psychrophilum* were adjusted to an optical density (OD) of 0.1 at 625 nm in 15 ml centrifuge tube. The TYES inoculated with *F. psychrophilum* (150 µl) was spread evenly on a TYES agar plate and allowed to absorb. The plates were divided in half and two vertical lines of 3 holes per plate were punched into the media using a 6 mm biopsy punch, deep enough to accommodate 100 µl in each well.

For each GI tract isolate to be screened, 500 µl was placed into 1.5 ml Eppendorf tubes and centrifuged at 3684×g at 4° C. for 5 minutes. In the first well (well A), 100 µl of sterile broth media was added. Isolate supernatant (100 µl) was added to well B and the isolate in its respective broth media (100 µl) was added to well C. The plates were then incubated at 15° C. for 24 to 48 hours. Once the *F. psychrophilum* lawn had grown, the zones of inhibition were measured, subtracting the diameter of the punched well.

Of the 234 isolates that were screened, 24 exhibited inhibitory activity against *F. psychrophilum* using both the supernatant (well B) as well as the broth culture (well C). In general, the supernatant did not show greater inhibition against *F. psychrophilum* than did the broth culture.

EXAMPLE 3

Identification of Bacterial Isolates

Bacterial isolates with inhibitory activity against *F. psychrophilum* were sent to the Washington Animal Disease Diagnostic Laboratory (WADDL) at Washington State University for a tentative identification using API® 20E and API® 20NE strips (BioMerieux, Marcy-l'Etoile, France). Of the 24 isolates sent to the WADDL, one (LR1-5) was unable to be identified by API 20E or API 20NE strips. The putative identification of the remaining 23 isolates is provided in Table 1.

TABLE 1

| Isolate | Source | Bacterial identification |
|---------|--------|--------------------------|
| 5-3.3 | Spring Valley | *Aeromonas sobria* |
| 5-3.5 | Spring Valley | *Plesiomonas shigelloides* |
| 5-3.6 | Spring Valley | *Hafnia alvei* |
| 5-3.14 | Spring Valley | *Aeromonas* sp. |
| 5-3.19 | Spring Valley | *Aeromonas sobria* |
| 5-4.17 | Spring Valley | *Aeromonas sobria* |
| 5-4.19 | Spring Valley | *Aeromonas sobria* |
| 5-6.2 | Spring Valley | *Aeromonas hydrophila* |
| 5-6.3 | Spring Valley | *Aeromonas sobria* |
| 5-6.5 | Spring Valley | *Aeromonas caviae* |
| 5-6.10 | Spring Valley | *Aeromonas sobria* |
| 5-6.12 | Spring Valley | *Plesiomonas shigelloides* |
| 5-6.16 | Spring Valley | *Aeromonas sobria* |
| 7-1.7 | Spring Valley | *Aeromonas caviae* |
| 7-1.15 | Spring Valley | *Aeromonas caviae* |
| 7-1.20 | Spring Valley | *Aeromonas caviae* |
| 7A-1.10 | Spring Valley | *Aeromonas caviae* |
| C6-6 | Fish Hatchery #1 | *Enterobacter* sp. |
| C6-8 | Fish Hatchery #1 | *Enterobacter* sp. |
| CS1-1 | Fish Hatchery #1 | *Citrobacter* sp. |
| CS3-5 | Fish Hatchery #1 | *Bacillus* sp. |
| LR1-5 | Fish Hatchery #2 | Unidentified |
| LR2-1 | Fish Hatchery #2 | *Pantoea* sp. |
| LR2-5 | Fish Hatchery #2 | *Pantoea* sp. |

EXAMPLE 4

Bacterial Colonization of Intestine

In vitro intestinal screening methods were adapted from Nikoskelainen et al, Applied and Environmental Microbiology, 67:2430-2435 (2001) and Cai et al, Journal of General and Applied Microbiology, 44:311-316 (1998). Isolates from frozen stock were inoculated into their respective broth media and allowed to grow for 48 hours at 15° C. The optical density of each isolate was adjusted to 0.1 OD at 625 nm to achieve a concentration of approximately $10^7$ colony-forming units (CFU) $ml^{-1}$. Duplicate 500 µl aliquots of each suspension were then centrifuged at 3684×g at 4° C. for 5 minutes with one pellet re-suspended in 1×PBS and the other in 1×PBS which contained 10% fish bile. Fish bile was collected by aseptically puncturing the gall bladders of rainbow trout and stored at −20° C. until use. Each sample was incubated at 15° C. for 1.5 hours and subsequently serially diluted and plated on their respective media using the drop plate method described in Chen, Journal of Microbiological Methods, 55:475-479 (2003). The bacterial colonies which grew on the plates were then enumerated after a period of 48 hours. Of the isolates screened, all 24 were able to survive a 1.5 hour exposure to 10% rainbow trout bile.

EXAMPLE 5

Test for Pathogenicity of Candidate Probiotics in Fish

Candidate probiotics, those showing inhibition toward *F. psychrophilum*, were grown to log phase in 20 ml of their respective media at 15° C. and subsequently harvested by centrifugation at 1600×g for 15 minutes at 15° C. The supernatant was poured off and the pellet was re-suspended with 1×PBS to obtain an OD of approximately 0.20 (±0.02) at 525 nm. Subsamples were taken to determine CFU $ml^{-1}$ using the drop plate method of Example 3, resulting in actual concentrations between $10^6$ and $10^7$ CFU $ml^{-1}$. Duplicate tanks of 10 fish weighing approximately 5 grams each were injected intraperitoneally (IP) with 25 µl of each candidate probiotic bacteria resulting in doses between $2.5 \times 10^4$ and $2.5 \times 10^5$ CFU $fish^{-1}$. Two control tanks containing 10 fish each received IP injections of 25 µl 1×PBS. Re-isolation of the probiotic from the kidney, liver and spleen was attempted by inoculation of organ tissues onto TYES agar from all mortalities as well as a subset of fish from each tank after a period of 28 days. Any probiotic producing mortality was eliminated from further consideration and testing.

Of the 24 isolates evaluated, eight were observed to cause direct mortality when injected into fish. Bacterial isolation from the kidney, liver or spleen was achieved for six of the eight isolates. No overt disease symptoms or mortalities were observed following injection of any of the other 16 candidate probiotics tested. Any candidate probiotic producing mortality was eliminated from further consideration and testing.

EXAMPLE 6

Effectiveness at Reducing Mortality Due to *F. psychrophilum*

Of the 16 candidate probiotics of Example 5 that did not produce overt symptoms or mortality, six candidates were eliminated for various reasons from further evaluation as a probiotic. The remaining ten candidate probiotics were evaluated for their ability in vivo to decrease mortality due to *F. psychrophilum* infection during four separate challenges.

EXAMPLE 6.1

For the first challenge, three candidate probiotic strains; C6-6, CS1-1, and 5-3.6, were evaluated.

This first trial utilized a positive control group (*F. psychrophilum* injection and no treatment), a mock infected group (1×PBS injection and no treatment), and three treatment groups (*F. psychrophilum* injection and probiotic treatment), with each group containing 80 fish. Prior to challenge, five fish (withheld from feed for 24 hours) were removed and sacrificed from each group to test for the existence of any candidate probiotic strains. The removed fish were euthanized using an overdose of tricaine methane sulfonate (MS-222®). After aseptically removing the mid and hind portions of the intestine (up to the pyloric caeca), the intestine was opened using a scalpel and swabbed using a sterile cotton swab. The swab was then used to streak TS and/or TYES agar plates for isolation of any bacteria present in the intestine. The three treatment groups and two control groups, now containing 75 fish each, were then separated into triplicate 25 fish groups and injection challenged subcutaneously with 25 μL of *F. psychrophilum* at $1.6 \times 10^6$ CFU fish$^{-1}$ or 1×PBS for the mock infected fish following the bacterial challenge procedures described in LaFrentz et al., Journal of Fish Diseases 25:703-713 (2002). At 72 hours post challenge, the positive control and mock infected groups were administered their respective feeds previously with each treatment group receiving one candidate probiotic through feed during the 28 day challenge.

While multiple bacterial species were isolated from the GI tract of the fish sacrificed prior to the introduction of candidate probiotics, none of these bacteria were identified as any of the candidate probiotic strains of interest. After day 28 of the challenge, mortality was observed in all groups with the exception of the mock infected fish and those treated with C6-6 which had 100% survival. Highest mortality was observed in groups treated with 5-3.6 (28%), CS1-1 (21.5%), and the positive controls (8%), respectively. Groups treated with candidate probiotics 5-3.6 and CS1-1 observed significantly higher ($P<0.05$) levels of mortality when compared to those treated with C6-6, and compared to positive control and mock infected groups.

EXAMPLE 6.2

For the second challenge, only candidate strain C6-6 was evaluated.

Prior to separating fish into treatment and control groups, five fish (withheld from feed for 24 hours) were removed and sacrificed to test for the existence of C6-6 as disclosed in Example 6.1. The fish were then separated into a positive control group (*F. psychrophilum* injection and no treatment), a mock infected group (1×PBS injection and no treatment), and two treatment groups (*F. psychrophilum* injection and probiotic treatment), each containing 48 fish. All fish were fed a standard trout diet until seven days prior to challenge. During this seven day period, one treatment group was fed C6-6 through oil dressed feed while the other C6-6 treatment group and the mock infected group received a standard trout diet without additives. The fish serving as the positive control group were fed a standard trout diet with the addition of menhaden oil. After this seven day period, fish were withheld from feed for 24 hours, separated into three groups of 16 fish each and challenged subcutaneously with 50 μL of *F. psychrophilum* at $7 \times 10^6$ CFU or 1×PBS for the mock infected fish as described by LaFrentz et al., (2002). Three days post infection with *F. psychrophilum*, the treatment group fed C6-6 prior to challenge and the mock infected group were administered a standard trout diet without the addition of menhaden oil while the positive control was fed a standard trout diet with the addition of menhaden oil. The second treatment group was then administered C6-6 through oil laden feed for the duration of the 28 day challenge period.

While multiple bacterial species were isolated from the GI tract of the fish sacrificed prior to the introduction of candidate probiotics, none of these bacteria were identified as any of the candidate probiotic strains of interest. After day 28 of the challenge, mortality was observed in all groups with the highest mortality (56%) being observed in the group fed C6-6 after injection with *F. psychrophilum*. In contrast, the group fed C6-6 prior to injection showed a reduction in mortality.

EXAMPLE 6.3

For the third challenge, three candidate strains, C6-8 (NRRL B-50482), LR2-1, and 7-1.20, were evaluated.

The third challenge utilized a positive control group (*F. psychrophilum* injection and no treatment) containing 85 fish, a mock infected group (1×PBS injection and no treatment) containing 80 fish, and three treatment groups (*F. psychrophilum* injection and probiotic candidate treatment) containing 85 fish each. Prior to challenge, five fish (withheld from feed for 24 hours) were removed and sacrificed from the control and treatment groups to test for the existence of any candidate probiotic strains being evaluated as disclosed in Example 6.1. All fish were fed a standard trout diet until 10 days prior to challenge. During this 10 day period, the treatment groups were fed one candidate probiotic through oil dressed feed with the mock infected group administered a standard trout diet without the addition of menhaden oil. The positive control was fed a standard trout diet with the addition of menhaden oil during this time. After this 10 day period, fish were withheld from feed for 24 hours, separated into triplicate 25 fish groups and challenged with *F. psychrophilum* using 25 μL subcutaneous injections at $3 \times 10^5$ CFU fish$^{-1}$ or 1×PBS for the mock infected fish as described by LaFrentz et al., (2002). Twenty-four hours post infection, feeding of the candidate probiotics resumed for the treatment groups with the mock infected group administered a standard trout diet without the addition of menhaden oil. The positive control continued to be fed a standard trout diet with the addition of menhaden oil during this time. The five remaining fish from each group were withheld from feed for an additional 48 hours and sacrificed to test for the presence of the candidate probiotic strains which were fed during the 10 day period.

While multiple bacterial species were isolated from the GI tract of the fish sacrificed prior to the introduction of candidate probiotics, none of these bacteria were identified as any of the candidate probiotic strains of interest. After day 28 of the challenge, mortality was observed in all groups with the exception of the mock infected group, as shown in FIG. 1, with the highest mortality being observed in the positive controls. Fish which were treated with candidate probiotic C6-8 resulted in significantly lower ($P<0.05$) cumulative percent mortality (44%) when compared to the positive control group (67%). Overall, fish fed C6-8 had a 34% decrease in mortality compared to the positive controls.

EXAMPLE 6.4

For the fourth challenge, five candidate strains, C6-6 (NRRL B-50481), 5-6.12, CS3-5, 5-3.3 and 5-3.5, were evaluated.

The fourth challenge utilized a positive control group (*F. psychrophilum* injection and no treatment) containing 85 fish, a mock infected group (1×PBS injection and no treatment) containing 80 fish, and five treatment groups (*F. psychrophilum* injection and probiotic treatment) containing 85 fish each. Prior to challenge, five fish (withheld from feed for 24 hours) were removed and sacrificed from the control and treatment groups to test for the existence of any candidate probiotic strains being evaluated as described in Example 6.1. All fish were fed a standard trout diet until 10 days prior to challenge. During this 10 day period, the treatment groups were fed one candidate probiotic through oil dressed feed with the mock infected group administered a standard trout diet without the addition of menhaden oil. The positive control was fed a standard trout diet with the addition of menhaden oil during this time. After this 10 day period, fish were withheld from feed for 24 hours, separated into triplicate 25 fish groups and challenged with *F. psychrophilum* using 25 μL subcutaneous injections at $3 \times 10^6$ CFU fish$^{-1}$ or 1×PBS for the mock infected fish as described by LaFrentz et al., (2002). Twenty-four hours post challenge, feeding of the candidate probiotics resumed for the treatment groups with the mock infected group administered a standard trout diet without the addition of menhaden oil. The positive control continued to be fed a standard trout diet with the addition of menhaden oil during this time. The five remaining fish from each group were withheld from feed for an additional 48 hours and sacrificed to test for the presence of the candidate probiotic strains which were fed during the 10 day period.

Figure 2:
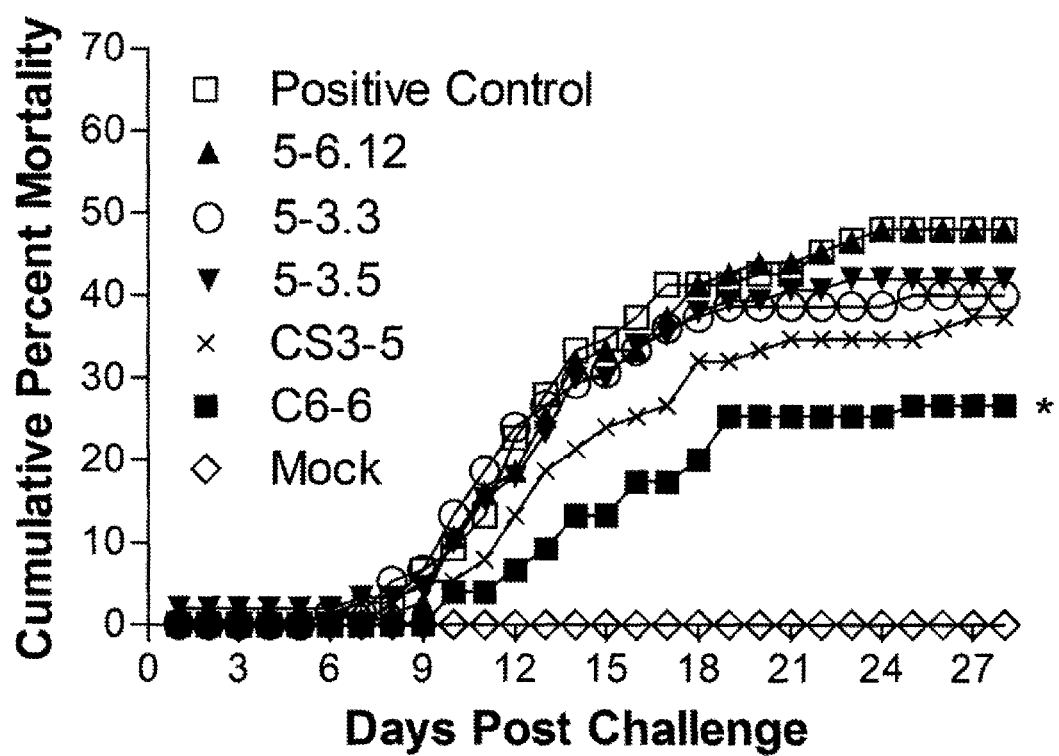
FIG. 2 is a graph showing % survival plotted against days post challenge for mock infected fish ($\diamond$) and for fish exposed to pathogenic Flavobacterium psychrophilum and then fed a feed containing candidate probiotic strain C6-6 ($\bullet$), CS3-5 (x), 5-3.5 ($\blacktriangledown$), 5-3.3 ($\bigcirc$), or 5-6.12 ($\blacktriangle$). Positive control ($\square$). * indicates significantly different from positive control ($p<0.05$).

While multiple bacterial species were isolated from the GI tract of the fish sacrificed prior to the introduction of candidate probiotics, none of these bacteria were identified as any of the candidate probiotic strains of interest. After day 28 of the challenge, mortality was observed in all groups with the exception of the mock infected group, as shown in FIG. 2. Highest mortality was observed in tanks treated with 5-6.12 (48%), as well as the positive controls (48%). Fish which were treated with candidate probiotics C6-6 resulted in significantly lower ($P<0.05$) cumulative percent mortality (26%) when compared to the positive control group (48%). Overall, fish fed C6-6 exhibited a 46% decrease in mortality compared to the positive controls.

EXAMPLE 7

In vitro Screening of Strain C6-6 Against Additional Pathogens

The in vitro tests described above in Example 2 were repeated utilizing probiotic strain C6-6 in order to determine whether this strain would inhibit the growth of a pathogen other than *F. psychrophilum*. Four days prior to testing, 10 ml of TYES broth was inoculated with *F. columnare*, the causative agent of Columnaris Disease. Columnaris Disease is an important disease in a wide variety of economically important fish species, including tilapia, carp, catfish, trout, flounder, and eels.

The TYES inoculated with *F. columnare* (150 μl) was spread evenly on a TYES agar plate and allowed to absorb. The plates were divided in half and two vertical lines of 3 holes per plate were punched into the media using a 6 mm biopsy punch, deep enough to accommodate 100 μl in each well.

500 μl of the broth was placed into 1.5 ml Eppendorf tubes and centrifuged at 3684×g at 4° C. for 5 minutes. In the first well (well A), 100 μl of sterile broth media was added. Supernatant (100 μl) containing the pathogen was added to well B and broth media (100 μl) containing the pathogen was added to well C. The plates were then incubated at 15° C. for 24 to 48 hours. Once the *F. columnare* lawn had grown, the zones of inhibition were measured, subtracting the diameter of the punched well.

The above procedure was performed in parallel utilizing *F. psychrophilum* for comparison. The tests showed that the zone of inhibition produced by C6-6 against *F. columnare* was comparable to and, in fact slightly greater than, that produced by strain C6-6 against *F. psychrophilum*.

Additionally, further modifications, uses, and applications of the invention described herein will be apparent to those skilled in the art. It is intended that such modifications be encompassed in the above description and in the following claims.

The invention claimed is:

1. An isolated bacterial strain selected from the group consisting of C6-6, which has been designated Accession number NRRL No. B-50481, and C6-8, which has been designated Accession number NRRL No. B-50482, which bacterial strains were deposited in accordance with the Budapest Treaty at the Agricultural Research Service Culture Collection (USDA, ARS, 1815 North University Street, Peoria, IL, 61064) on Mar. 23, 2011.

2. The isolated bacterial strain of claim 1 which is C6-6.

3. The isolated bacterial strain of claim 1 which is C6-8.

4. A feed for fish comprising either or both of bacterial strain C6-6, which has been designated Accession number NRRL No. B-50481, and bacterial strain C6-8, which has been designated Accession number NRRL No. B-50482, which bacterial strains were deposited in accordance with the Budapest Treaty at the Agricultural Research Service Culture Collection (USDA, ARS, 1815 North University Street, Peoria, IL, 61064) on Mar. 23, 2011.

5. The fish feed of claim 4 which comprises bacterial strain C6-6.

6. The fish feed of claim 4 which comprises bacterial strain C6-8.

7. The fish feed of claim 4 which comprises bacterial strain C6-6 and bacterial strain C6-8.

* * * * *